United States Patent [19]

Kranzler et al.

[11] Patent Number: 5,098,779
[45] Date of Patent: Mar. 24, 1992

[54] CARVABLE IMPLANT MATERIAL

[75] Inventors: Thane L. Kranzler; Norman J. Sharber, both of Flagstaff, Ariz.

[73] Assignee: W. L. Gore & Associates, Inc., Newark, Del.

[21] Appl. No.: 543,240

[22] Filed: Jun. 25, 1990

[51] Int. Cl.$^5$ .............................. B32B 9/00; A61F 2/28
[52] U.S. Cl. .................................. 428/306.6; 428/308.4; 428/315.5; 428/422; 623/11; 623/16
[58] Field of Search ............... 428/306.6, 308.4, 315.5, 428/422; 623/11, 16

[56] References Cited

U.S. PATENT DOCUMENTS

| | | | |
|---|---|---|---|
| 3,272,204 | 9/1966 | Artandi et al. | 606/229 |
| 3,276,448 | 10/1966 | Kronenthal | 606/229 |
| 3,992,725 | 11/1976 | Homsy | 623/11 |
| 4,129,470 | 12/1978 | Homsy | 156/155 |
| 4,385,093 | 5/1983 | Hubis | 428/422 |
| 4,772,285 | 9/1988 | Ksander | 623/8 |
| 5,032,445 | 7/1991 | Scantlebury et al. | 428/422 |

Primary Examiner—William J. Van Balen
Attorney, Agent, or Firm—Wayne D. House

[57] ABSTRACT

A carvable implant material for use in surgery and especially in plastic and reconstructive surgery is described which comprises porous PTFE having a coating of a stiffening agent intended to stiffen the PTFE in order to render it carvable. This material may thus be carved into a desired shape prior to implantation. The stiffening agent is biodegradable to allow tissue ingrowth to stabilize the location of the implant as the biodegradable stiffening agent is degraded and absorbed by the body.

22 Claims, 2 Drawing Sheets

CARVABLE IMPLANT MATERIAL

FIELD OF THE INVENTION

This invention relates to a carvable porous polytetrafluoroethylene implant material for use in plastic and reconstructive surgery and to a method for making such an implant material.

BACKGROUND OF THE INVENTION

Plastic and reconstructive surgery often requires the use of graft materials for the replacement or augmentation of tissues. Materials used for this purpose heretofore have been of biologic or synthetic origin. Biologic materials of both autologous and homologous origin have been tried extensively. Both types of biologic material have been subject to unpredictable resorption, requiring the patient to undergo additional corrective surgery. The use of homologous implant materials, for example, collagen or bone, can also result in an adverse immunologic reaction that can lead to graft rejection and extrusion. While such adverse reactions do not occur with autologous implants, the use of autologous material involves additional surgical time and trauma for their removal.

Synthetic materials previously used for implantation have generally been polymeric, for example, silicone and polytetrafluoroethylene (hereinafter PTFE). Nonporous materials do not allow tissue ingrowth and as a consequence are known to migrate from the implant location. Preferred synthetic materials have a porous structure that promotes tissue ingrowth and stabilization of the implanted material.

Proplast®, a carvable porous composite implant material comprising PTFE fibers, powdered PTFE resin and carbon or aluminum oxide, has been available for some time. This material and its methods of manufacture are described in U.S. Pat. Nos. 3,992,725 and 4,129,470. Briefly, this material is made by blending the above listed materials with a soluble filler, filtering the blend to produce a cake, pressing and heating the cake, drying the cake, sintering the cake, and finally leaching out the filler material and again drying the resulting porous composite. This implant material is carvable and allows tissue ingrowth. However, the use of carbon or aluminum oxide in this material increases its tissue reactivity, potentially resulting in undesirable complications such as encapsulation by fibrous tissue, erosion of overlying tissues and extrusion. Finally, the carbon impregnated material is often visible through the skin when implanted subcutaneously in light-skinned patients.

Pure PTFE, that is, PTFE without other added materials such as carbon, has a long history of use as an implantable material because it is one of the least reactive materials known. In porous form it can allow tissue ingrowth. Porous PTFE has been available for some time in a form known as expanded PTFE. The manufacture of this material is described in U.S. Pat. Nos. 3,953,566, 3,962,153 and 4,187,390. Expanded PTFE has a microstructure characterized by nodes interconnected by fibrils. This material has a history of use in such implant applications as vascular grafts, sutures and structural soft tissue repair including hernia repair and ligament augmentation and replacement. The porosity and microstructure of expanded PTFE can be varied to produce different permeability characteristics for use in a variety of applications.

Many implantable biodegradable synthetic polymers have been investigated and applied in various applications including the controlled time release of drugs and for medical devices such as sutures, prosthetic ligaments and bone repair. These polymers and their copolymers are chosen for specific applications according to their strength characteristics and their known rates of degradation. Their success in these applications is largely due to the following characteristics:
1) Adequate mechanical strength;
2) Controlled rate of degradation;
3) Complete absorbability without formation of toxic metabolites; and
4) Minimal inflammatory response from the host.

Frequently used implantable biodegradable synthetic homopolymers include polydioxanone (PDS), polyglycolic acid (PGA, also known as polyhydroxyacetic ester), polylactic acid (PLA) and polycaprolactone.

Copolymers of PGA/PLA are also commonly used. Copolymers of PGA/PLA typically degrade faster than either homopolymer PGA or PLA. Degradation rate is affected by the blend of the copolymer, the degree of crystallinity of the polymers, and the addition of other agents. The PGA degradation rate may also be sensitive to the rate of curing of the polymer, the fast-cured polymer appearing to degrade more quickly than the slow-cured.

In addition to synthetic polymeric materials, several biologically derived materials have been used for implantable biodegradable applications. Such biologically derived materials include albumin and collagen.

SUMMARY OF THE INVENTION

A carvable implant material for use in surgery and especially in plastic and reconstructive surgery is described. The material comprises porous PTFE having a coating of a biocompatible stiffening agent to render the porous PTFE adequately rigid for carving. The coating is preferably applied in a manner that allows the porous PTFE to become impregnated by the stiffening agent. The stiffening agents used herein are biodegradable materials including synthetic biodegradable polymers and biologically derived materials which allow the ingrowth of tissue into the porous PTFE after the stiffening agent is degraded through absorption.

DETAILED DESCRIPTION OF THE INVENTION

Figure 1:
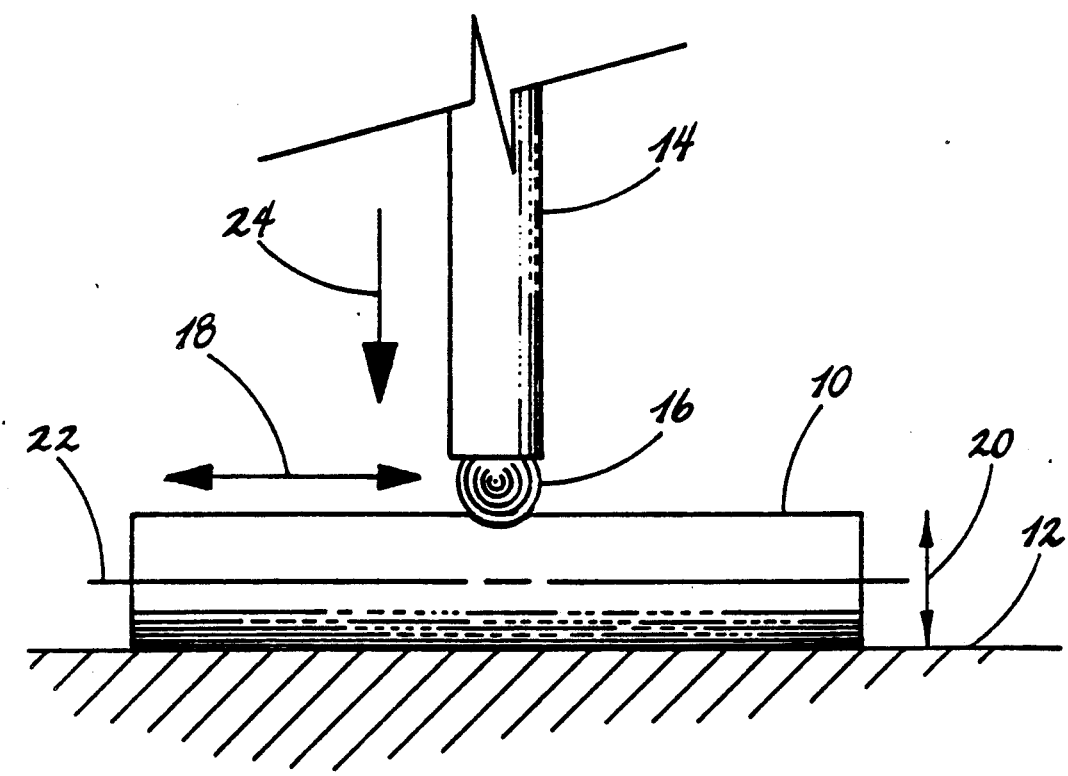
FIG. 1 describes a hardness test performed on a rod-shaped sample as a measure of carvability.

The ideal material for use in plastic and reconstructive surgery must be biocompatible and should be porous to allow tissue attachment and ingrowth to prevent migration of the material. It would have a texture similar to living tissue, that is, after implantation the implant material does not feel discontinuous with the surrounding tissue. Finally, it must be capable of being readily shaped to the desired contour.

Pure, porous PTFE possesses all of the above attributes with the exception of the ability to be readily shaped. It cannot be shaped by compression as the porosity and tissue ingrowth characteristic of the material will be severely compromised. The inherent softness of this material makes it very difficult to carve to a desired shape.

It has been found possible to render porous PTFE carvable by coating it with a biodegradable stiffening agent before implantation. The coating can be allowed to penetrate the pores of the PTFE so that the porous microstructure of nodes and fibrils becomes coated with the stiffening agent. The agent can be allowed to fill all or part of the interior space available within the porous structure. Conversely, the penetration of the stiffening agent can be limited to the outer portions of the available thickness of porous PTFE if only a limited amount of shaping is desired. In this instance the stiffening agent can be applied essentially as a surface coating.

Carvable is herein intended to mean capable of being carved to a desired shape with the use of a sharp blade. Porous PTFE typically compresses under the pressure of a sharp blade and so does not lend itself to being carved. The use of a stiffening agent to coat or impregnate the porous structure of the porous PTFE gives the material enough rigidity to render it carvable.

The stiffening agent used in the present invention is absorbable by the body in which it is implanted, that is, biodegradable. Consequently the implant material of the present invention recovers its original (before coating), inherent softness after it has been carved, implanted in a living body, and the stiffening agent absorbed by the living body.

Suitable biodegradable stiffening agents include biologically derived materials such as collagen and albumin, and synthetic polymers such as PLA, PGA, PGA/PLA copolymer, PDS and polycaprolactone.

The coating of absorbable stiffening agent is preferably applied to the porous PTFE by soaking the PTFE in a solution of the agent and an appropriate solvent. The soaking time depends on the ability of the mixture to penetrate the porous PTFE and the depth of penetration required. A vacuum may be used to aid penetration. Heating the mixture may also improve the penetrating ability of some solvent/stiffening agent solutions. The coated porous PTFE is then air dried to remove the solvent, with or without the application of heat. Finally and optionally, the coated porous PTFE is baked until the coating is melted in order to increase the rigidity of the porous PTFE.

Suitable stiffening agents and solvents may be selected from a range of materials familiar to those skilled in the art of biocompatible biodegradable materials.

The degree of rigidity of the porous PTFE can be varied during manufacture of the coated porous PTFE. Factors that influence this rigidity include the porosity and fibril length of the PTFE, the amount of heat applied during manufacture of the porous PTFE, the stiffening agent chosen, the amount of internal space filled by the stiffening agent and the depth of penetration of the stiffening agent.

As no standard exists for measuring carvability that these inventors are aware of, carvability was subjectively compared to the percent increase in weight of expanded PTFE samples impregnated with stiffening agents. Carvability was further compared to hardness measurements made on impregnated, carvable samples and unimpregnated, non-carvable samples. It was determined that percent weight gains on the order of as little as about 1% were more than enough to render the PTFE carvable. Levels of 2 to 3% were still more easily carved and are thus considered preferable. Levels in excess of about 3% seemed to offer no further increase in ease of carvability.

The hardness test of Example 3 below indicates that a force greater than 0.6 kg shows that the material is adequately hard to be carvable. As the samples tested containing the least amount of stiffening agent (1% by weight of PGA/PLA copolymer) were more than minimally carvable, it is believed that smaller amounts of stiffening agent would represent the minimum for practical carvability. Less than 1% stiffening agent by weight will have a hardness force value less than the 0.6 kg described above. It is believed that a hardness force value of about 0.4 kg will indicate the minimum hardness necessary for carvability.

EXAMPLE 1

PTFE resin (Fluon ® CD-123 obtained from ICI Americas, Inc., Wilmington, DE) was blended with about 320cc of "Isopar ®M" odorless solvent (obtained from Exxon Corporation, Houston, TX) per kg of PTFE, compressed into a tubular billet, heated to 40° C. and extruded into a 10 mm O.D. rod in a ram extruder having a reduction ratio of about 50.8:1 in cross sectional area from billet to the extruded rod. The extrudate was then placed into an oven set at about 300° C. and stretched about 3.89:1 (a 289% increase in length) at a rate of about 280%/second (percent change in length divided by stretching time) to produce porous, expanded PTFE rods.

The expanded rods were then restrained from shrinking and heated in a second oven set at approximately 365° C. for a total of 22 minutes, thereby sintering the rod. The expanded rod material was then cut into 10 cm lengths and each sample was weighed Next, eight grams of 50/50 D,L-lactide/glycolide (Medisorb ®, Lot #591655046, available from E.I. duPont de Nemours & Co., Inc., Wilmington, DE) were placed into a wide-mouth bottle. Methylene chloride was added to make a 10:1 solution (volume of methylene chloride to weight of copolymer) and the bottle sealed. The mixture was stirred continuously with a magnetic stirrer for several hours until the copolymer was completely in solution. A 10 cm segment of the described rod material was placed in a 60 cc syringe along with about 40 ml of the above solution. The syringe was held with the open end pointed up, and all air was expelled from the syringe by applying pressure with the syringe plunger. The open end of the syringe was then occluded and the plunger was retracted creating a vacuum. The syringe was then uncovered and the resulting air bubble was expelled. This process was repeated several times until the air was removed from the expanded PTFE rod and replaced by the solution. The resulting D,L-lactide/glycolide impregnated rod was then removed from the syringe and allowed to dry overnight. After drying, the impregnated rods formed rigid, carvable material.

The impregnated rods were weighed individually after drying to determine the amount of weight gain as follows:

$$\left[ \frac{\text{Weight after impregnation}}{\text{Weight before impregnation}} \times 100\% \right] - 1 = \%\text{ Weight Gain}$$

Typical weight gain for these samples was about 10%. Impregnated rod samples were then individually submerged in methylene chloride for various periods of time and subsequently allowed to dry. These were o weighed again to determine a new percent weight gain. In this manner, expanded PTFE rods with a range of percent weight gains were created. Samples were created having weight gains of 1%, 2%, 3%, 4%, 5% and 10%. All of these samples were determined to be adequately rigid to be carvable. Unimpregnated control samples were not carvable.

The hardness of the copolymer impregnated rods was measured and compared to that of unimpregnated control rods using a model 4201 Instron testing machine. For this test, a 3.175 mm diameter steel ball (16) was attached to a post (14) and was driven into the surface (10) of the rod to be tested along a rod diameter (20) and perpendicular to the direction of the fibrils (18). The ball (16) and post (14) were driven downward (24) by the Instron at a rate of 10 mm/min perpendicular to a flat surface (12) while the rod sample (10) lay on the flat surface (12) with its longitudinal axis (22) parallel to the flat surface (12). The force required to indent each sample 1.00 mm was recorded from the Instron chart recorder; these data are shown in Table 1. It should be noted that the hardness of all impregnated, carvable samples was substantially greater than the hardness of the unimpregnated, non-carvable samples.

TABLE 1

| Hardness (n = 3 for each % wt gain) | |
|---|---|
| % wt gain of sample | force (kg) to indent 1.00 mm |
| 10% | 3.78 |
| 5% | 3.42 |
| 4% | 3.32 |
| 3% | 2.36 |
| 2% | 2.12 |
| 1% | 1.45 |
| 0% | 0.08 |

EXAMPLE 2

Ten grams of powdered bovine albumin (bovine albumin, fraction V, 6–99% albumin, Lot #58F-0021, Sigma Chemical Co., St. Louis, MO) was dissolved in 50 ml of 7.2 pH phosphate buffer in distilled water. An additional 4 ml of a surfactant (liquid dish detergent) was added to the solution. Expanded PTFE rods, described in Example 1, approximately 10 cm long, were placed in a 60 cc syringe along with the albumin/buffer/surfactant solution. The expanded PTFE material was then impregnated using the syringe vacuum technique described in Example 1. The impregnated expanded PTFE rods were then placed in a 6.5% glutaraldehyde solution for 2 hours with constant stirring. The samples were then rinsed in 7.2 pH buffered saline for one hour with constant stirring. Samples were then allowed to dry overnight, forming rigid, carvable material. Four expanded PTFE impregnated rods had average weight gains of 13.3%. Three of these samples were randomly selected for hardness testing as performed in Example 1. Hardness (indented 1.00 mm by a 3.175 mm diameter ball at a rate of 10 mm/min) measured an average of 1.69 kg.

EXAMPLE 3

Eight grams of 50/50 D,L-lactide/glycolide (DuPont Medisorb) was placed into a wide-mouth jar. Eighty milliliters of methylene chloride was then added to the container and the container sealed. The mixture then stirred continuously for several hours until the copolymer was completely in solution. GORE-TEX® Soft Tissue Patch material of 2 mm thickness, a porous expanded PTFE material available from W. L. Gore and Associates, Inc., Flagstaff, AZ was cut into discs of about 5 cm diameter. These discs were placed, one at a time in rolled up form, into a 60 cc syringe along with about 40 ml of the above solution. The discs were impregnated with the D,L-lactide/glycolide solution as described in Example 1. The discs were then unrolled, covered with a 1 kg weight to hold them flat, and allowed to dry overnight. The resulting discs were stiff and carvable. The average weight gain for eight 2 mm GORE-TEX Soft Tissue Patch discs was 17.5%.

Figure 2:
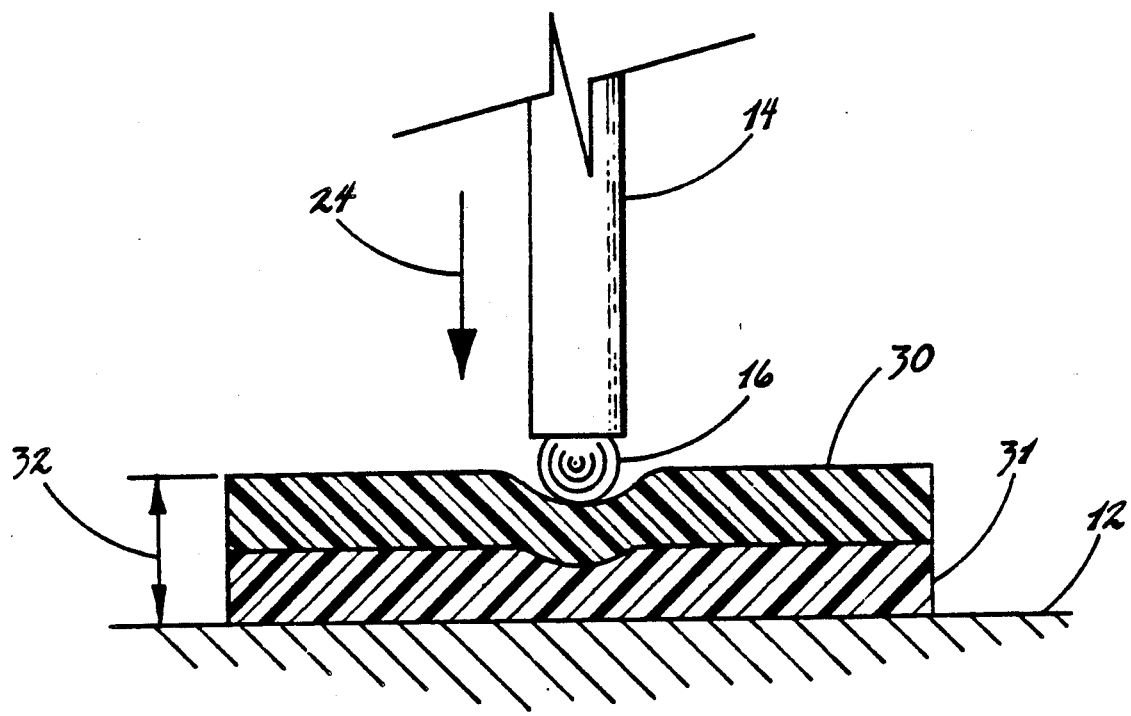
FIG. 2 describes a hardness test performed on samples in the form of sheets as a measure of carvability.

As shown by FIG. 2, the hardness of these samples was tested in the same manner as described in Example 1 except that 2 samples (30 and 31) were stacked to provide a thickness (32) of 4 mm to be indented by the steel ball (16). The results are shown in Table 2.

TABLE 2

| Hardness (n = 3 for each % wt gain) | |
|---|---|
| % wt gain of sample | force (kg) to indent 1.00 mm |
| 4% | 1.23 |
| 3% | 1.10 |
| 2% | 0.86 |
| 1% | 0.61 |
| 0% | 0.06 |

The hardness data for the GORE-TEX Patch material of Example 3 is somewhat different from that of the rod material of Example 1. The differences are believed to be a result of the different processing received by the two different forms of expanded PTFE prior to impregnation with the stiffening agents. Both forms exhibited substantial differences in hardness forces between unimpregnated, non-carvable versions and their otherwise equivalent 1% weight gain impregnated, carvable versions.

We claim:

1. A porous implant material, carvable at room temperature, comprising porous polytetrafluoroethylene having one or more outer surfaces and interior porous surfaces, and having a coating of a biocompatible biodegradable stiffening agent that renders the porous polytetrafluoroethylene adequately rigid for carving.

2. The carvable implant material of claim 1 containing at least about 1% by weight of a biocompatible biodegradable stiffening agent.

3. The carvable implant material of claim 1 containing at least about 2% by weight of a biocompatible biodegradable stiffening agent.

4. The carvable implant material of claim 1 containing at least about 3% by weight of a biocompatible biodegradable stiffening agent.

5. The carvable implant material of claim 1 containing at least about 5% by weight of a biocompatible biodegradable stiffening agent.

6. The carvable implant material of claim 1 wherein the porous polytetrafluoroethylene is expanded polytetrafluoroethylene having a microstructure of nodes and fibrils.

7. The carvable implant material of claim 6 having a hardness force measurement of greater than about 0.4 kg when a sample of at least 4 mm thickness is indented for a distance of 1.0 mm by a ball of 3.175 mm diameter at a rate of 10 mm/min in a direction perpendicular to the direction of the fibrils.

8. The carvable implant material of claim 6 having a hardness force measurement of greater than about 0.6 kg when a sample of at least 4 mm thickness is indented for a distance of 1.0 mm by a ball of 3.175 mm diameter at a rate of 10 mm/min in a direction perpendicular to the direction of the fibrils.

9. The carvable implant material of claim 6 having a hardness force measurement of greater than about 0.86 kg when a sample of at least 4 mm thickness is indented for a distance of 1.0 mm by a ball of 3.175 mm diameter at a rate of 10 mm/min in a direction perpendicular to the direction of the fibrils.

10. The carvable implant material of claim 6 wherein the biodegradable stiffening agent is a biologically derived material.

11. The carvable implant material of claim 6 wherein the biodegradable stiffening agent is albumin.

12. The carvable implant material of claim 6 wherein the biodegradable stiffening agent is collagen.

13. The carvable implant material of claim 6 wherein the coating primarily covers the outer surface of the porous polytetrafluoroethylene.

14. The carvable implant material of claim 6 wherein the coating covers at least part of the interior porous surfaces of the porous polytetrafluoroethylene.

15. The carvable implant material of claim 6 wherein the stiffening agent is comprised of a synthetic biodegradable material.

16. The carvable implant material of claim 15 wherein the synthetic biodegradable stiffening agent is selected from the group consisting of polylactic acid, polyglycolic acid, polydioxanone and polycaprolactone.

17. The carvable implant material of claim 15 wherein the synthetic biodegradable stiffening agent is a copolymer of polylactic acid and polyglycolic acid.

18. A process of manufacturing the carvable implant material of claim 1 comprising:
   a) coating the outer surface of the carvable implant material with a liquid stiffening agent,
   b) drying the stiffening agent.

19. The process of claim 18 where the stiffening agent is diluted with a solvent before coating the carvable implant material.

20. A process of manufacturing the carvable implant material of claim 1 comprising:
   a) diluting the stiffening agent with a solvent to allow the diluted stiffening agent to penetrate the porous structure of the porous polytetrafluoroethylene;
   b) coating the carvable implant material by a means for coating suitable for allowing the dilute stiffening agent to coat at least part of the interior porous surfaces of the porous polytetrafluoroethylene;
   c) drying the stiffening agent.

21. The process of claim 20 wherein the means for coating comprises soaking the carvable implant material in the diluted stiffening agent.

22. The process of claim 21 wherein the means for coating includes the application of a vacuum to the porous polytetrafluoroethylene.

* * * * *